(12) United States Patent
Sargent

(10) Patent No.: US 6,443,157 B1
(45) Date of Patent: Sep. 3, 2002

(54) MEDICAL BACKBOARD APPARATUS

(76) Inventor: David T. Sargent, 9134 S. Cripple Creek Cir., West Jordan, UT (US) 84088

( * ) Notice: Subject to any disclaimer, the term of this patent is extended or adjusted under 35 U.S.C. 154(b) by 0 days.

(21) Appl. No.: 09/881,875

(22) Filed: Jun. 15, 2001

(51) Int. Cl.⁷ .............................................. A61B 19/00
(52) U.S. Cl. ......................................... 128/870; 5/625
(58) Field of Search ................................ 602/2, 35–36, 602/19, 14; 128/870, 846, 877; 5/625, 628; D24/190

(56) References Cited

U.S. PATENT DOCUMENTS

| | | | |
|---|---|---|---|
| 3,707,734 A | | 1/1973 | Matthews |
| 4,369,982 A | * | 1/1983 | Hein et al. .............. 280/47.131 |
| 4,655,206 A | * | 4/1987 | Moody ........................ 128/870 |
| 5,048,134 A | | 9/1991 | Dennill et al. |
| 5,060,425 A | * | 10/1991 | Kappers et al. ............... 52/36.4 |
| 5,094,418 A | * | 3/1992 | McBarnes et al. ........ 248/125.1 |
| D328,351 S | | 7/1992 | Ott |
| 5,154,186 A | | 10/1992 | Laurin et al. |
| 5,749,374 A | * | 5/1998 | Schneider, Sr. ............. 128/870 |
| 5,774,916 A | * | 7/1998 | Kurhi ............................. 5/632 |
| D403,423 S | | 12/1998 | Bologovsky et al. |
| 5,950,627 A | | 9/1999 | Bologovsky et al. |
| 6,151,730 A | * | 11/2000 | Weston .......................... 5/110 |
| 6,155,260 A | * | 12/2000 | Lavin et al. ................. 128/845 |
| 6,175,977 B1 | * | 1/2001 | Schumacher et al. ......... 12/209 |

* cited by examiner

Primary Examiner—Denise M. Pothier
Assistant Examiner—Quang D Thanh

(57) ABSTRACT

A medical backboard apparatus for providing improved patient care. The medical backboard apparatus includes a board assembly including a board member having a top, a bottom, a head portion, and a foot portion, and also having a plurality of hand-hold slots being spaced along a perimeter thereof and being disposed therethrough; and also includes a board support member being attached to the board member; and further includes a head fastening assembly being connected to the board member for restraining a person's head upon the board member; and also includes an elongate intravenous feeding support member being pivotally attached to the board member; and further includes heating elements including a power line being disposed in the board member; and also includes a defibrillating assembly being attached to the board member.

10 Claims, 3 Drawing Sheets

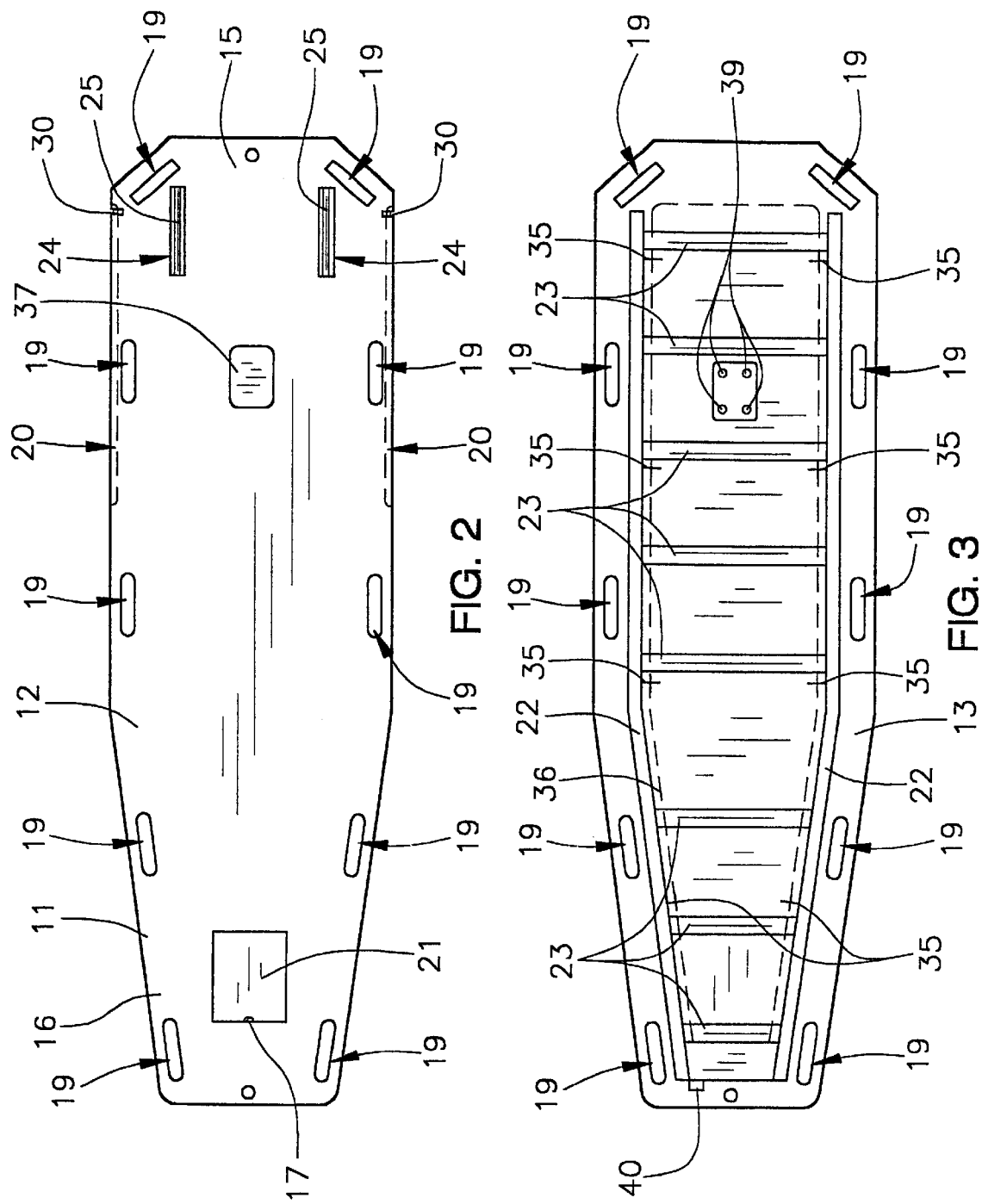

MEDICAL BACKBOARD APPARATUS

BACKGROUND OF THE INVENTION

1. Field of the Invention

The present invention relates to medical restraining board assemblies and more particularly pertains to a new medical backboard apparatus for providing improved patient care.

2. Description of the Prior Art

The use of medical restraining board assemblies is known in the prior art. More specifically, medical restraining board assemblies heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,154,186; U.S. Pat. No. 5,048,134; U.S. Pat. No. 5,950,627; U.S. Pat No. 3,707,734; U.S. Pat. No. Des. 403,423; and U.S. Pat. No. Des. 328,351.

While these devices fulfill their respective, particular objectives and requirements, the aforementioned patents do not disclose a new medical backboard apparatus. The inventive device includes a board assembly including a board member having a top, a bottom, a head portion, and a foot portion, and also having a plurality of hand-hold slots being spaced along a perimeter thereof and being disposed therethrough; and also includes a board support member being attached to the board member; and further includes a head fastening assembly being connected to the board member for restraining a person's head upon the board member; and also includes an elongate intravenous feeding support member being pivotally attached to the board member; and further includes heating elements including a power line being disposed in the board member; and also includes a defibrillating assembly being attached to the board member.

In these respects, the medical backboard apparatus according to the present invention substantially departs from the conventional concepts and designs of the prior art, and in so doing provides an apparatus primarily developed for the purpose of providing improved patient care.

SUMMARY OF THE INVENTION

In view of the foregoing disadvantages inherent in the known types of medical restraining board assemblies now present in the prior art, the present invention provides a new medical backboard apparatus construction wherein the same can be utilized for providing improved patient care.

The general purpose of the present invention, which will be described subsequently in greater detail, is to provide a new medical backboard apparatus which has many of the advantages of the medical restraining board assemblies mentioned heretofore and many novel features that result in a new medical backboard apparatus which is not anticipated, rendered obvious, suggested, or even implied by any of the prior art medical restraining board assemblies, either alone or in any combination thereof.

To attain this, the present invention generally comprises a board assembly including a board member having a top, a bottom, a head portion, and a foot portion, and also having a plurality of hand-hold slots being spaced along a perimeter thereof and being disposed therethrough; and also includes a board support member being attached to the board member; and further includes a head fastening assembly being connected to the board member for restraining a person's head upon the board member; and also includes an elongate intravenous feeding support member being pivotally attached to the board member; and further includes heating elements including a power line being disposed in the board member; and also includes a defibrillating assembly being attached to the board member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new medical backboard apparatus which has many of the advantages of the medical restraining board assemblies mentioned heretofore and many novel features that result in a new medical backboard apparatus which is not anticipated, rendered obvious, suggested, or even implied by any of the prior art medical restraining board assemblies, either alone or in any combination thereof.

It is another object of the present invention to provide a new medical backboard apparatus which may be easily and efficiently manufactured and marketed.

It is a further object of the present invention to provide a new medical backboard apparatus which is of a durable and reliable construction.

An even further object of the present invention is to provide a new medical backboard apparatus which is susceptible of a low cost of manufacture with regard to both materials and labor, and which accordingly is then susceptible of low prices of sale to the consuming public, thereby making such medical backboard apparatus economically available to the buying public.

Still yet another object of the present invention is to provide a new medical backboard apparatus which provides in the apparatuses and methods of the prior art some of the advantages thereof, while simultaneously overcoming some of the disadvantages normally associated therewith.

Still another object of the present invention is to provide a new medical backboard apparatus for providing improved patient care.

Yet another object of the present invention is to provide a new medical backboard apparatus which includes a board assembly including a board member having a top, a bottom, a head portion, and a foot portion, and also having a plurality of hand-hold slots being spaced along a perimeter thereof and being disposed therethrough; and also includes a board support member being attached to the board member; and further includes a head fastening assembly being connected to the board member for restraining a person's head upon the board member; and also includes an elongate intravenous feeding support member being pivotally attached to the board member; and further includes heating elements including a power line being disposed in the board member; and also includes a defibrillating assembly being attached to the board member.

Still yet another object of the present invention is to provide a new medical backboard apparatus that is easy and convenient to use during emergency situations.

Even still another object of the present invention is to provide a new medical backboard apparatus that is versatile and provides many of the necessities needed for attending to an injured person.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a top plan view of the present invention.

FIG. 3 is a bottom plan view of the present invention.

DESCRIPTION OF THE PREFERRED EMBODIMENT

Figure 1:
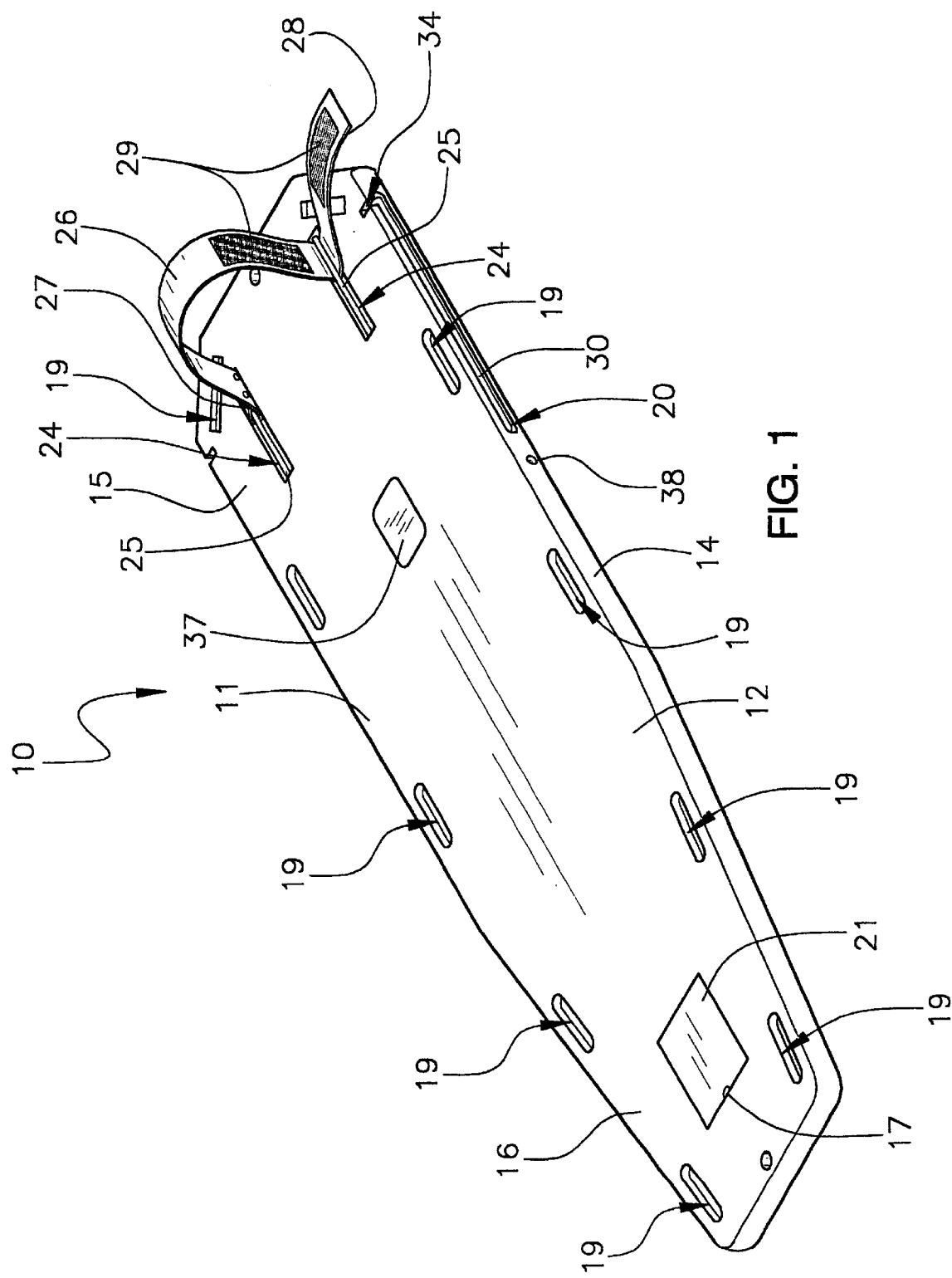
FIG. 1 is a perspective view of a new medical backboard apparatus according to the present invention.
Figure 4:
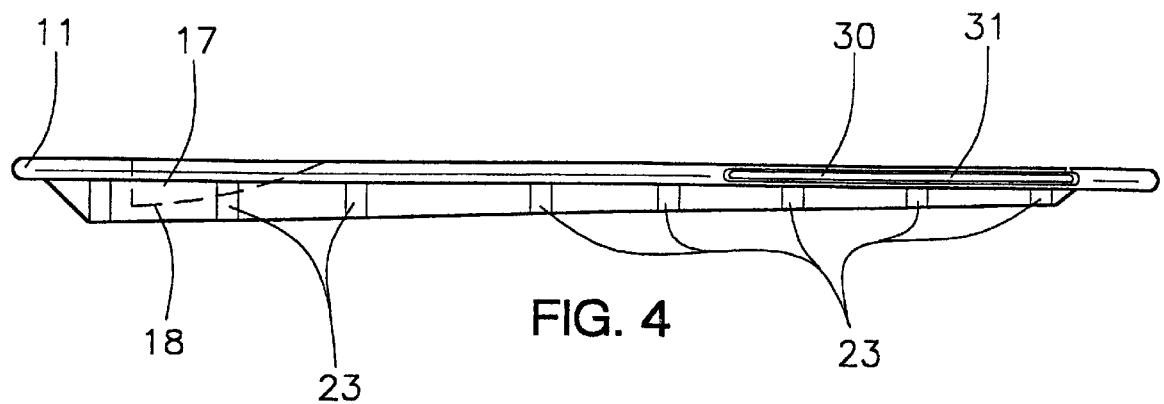
FIG. 4 is a side elevational view of the present invention.
Figure 5:
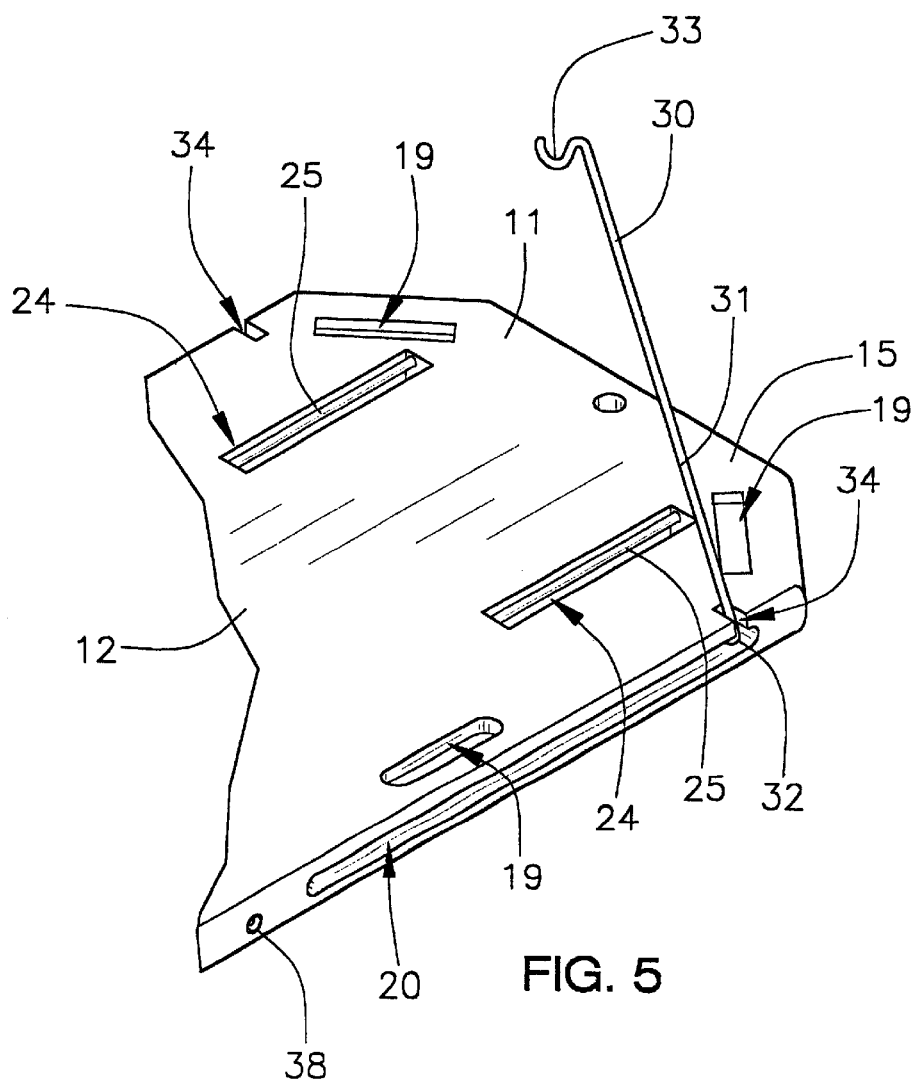
FIG. 5 is a partial perspective view of the present invention.

With reference now to the drawings, and in particular to FIGS. 1 through 5 thereof, a new medical backboard apparatus embodying the principles and concepts of the present invention and generally designated by the reference numeral 10 will be described.

As best illustrated in FIGS. 1 through 5, the medical backboard apparatus 10 generally comprises a board assembly including a board member 11 having a top 12, a bottom 13, a head portion 15, and a foot portion 16, and also having a plurality of hand-hold slots 19 being spaced along a perimeter thereof and being disposed therethrough. The board member 11 further includes a storage/cradle compartment 17 being disposed in the foot portion 16 thereof, and also includes an elongate slots 20 being disposed in side edges 14 and in the head portion 15 of the board member 11, and further includes a notches 34 being disposed in the top 12 of the board member 11 and in the elongate slots 20 at ends thereof. The foot portion 16 of the board member 11 is tapered toward a foot end thereof, and the head portion includes a multi-sided head edge. The backboard assembly further includes a cover member 21 being removably disposed over the storage/cradle compartment 17. The storage/cradle compartment 21 has a slanted bottom wall 18 to prevent an oxygen tank from sliding off the board member 11. The board member 11 has a length of approximately 6 feet and has a width of approximately 12 to 16 inches and also has a thickness of approximately 1½ to 3 inches.

A board support member 22, 23 is conventionally attached to the board member 11. The board support member 22, 23 includes a pair of elongate side support members 22 being securely and conventionally attached to the bottom 13 along a side perimeter thereof, and also includes a plurality of cross members 23 being securely and conventionally attached to and disposed between the elongate side support members 22 with the cross members 23 being gradually thicker toward the foot portion 16 of the board member 11. The cross members 23 have a thickness ranging from 1¾ inches to 3 inches.

A head fastening assembly is conventionally connected to the board member 11 for restraining a person's head upon the board member 11. The head fastening assembly includes longitudinal slots 24 being spaced apart and being disposed through the head portion 15 of the board member 11, and also includes elongate strap support members 25 being securely and conventionally disposed in the longitudinal slots 24, and further includes a strap member 26 having a first end 27 being looped about one of the elongate support strap members 25 and also having a second end portion 28 which is looped about another of the elongate strap support members 25 and being fastenable upon itself, and also includes strips of hook and loop fasteners 29 being securely and conventionally attached along a portion of the second end portion 28 of the strap member 26 for fastening the strap member 26 upon itself with the strap member 26 being adapted to secure a person's head to the board member 11.

A pair of elongate intravenous feeding support members 30 are pivotally attached to the board member 11. The elongate intravenous feeding support members 30 are pivotally and removably received in the elongate slots 20 with each having a shaft portion 31 which is removably disposed through the respective notch 34 and also having a first end 32 which is angled relative to the shaft portion 31 and which is pivotally received in the respective elongate slot 20 and further having an arcuate hook-shaped second end 33 which is adapted to support an intravenous feeding member. Heating elements 35 including a power line 36 and a power switch 40 being conventionally connected to the power line 36 are conventionally disposed in the board member 11. The heating elements 35 and the power line 36 are disposed along the perimeter of the board member 11.

A defibrillating assembly is conventionally attached to the board member 11. The defibrillating assembly includes a defibrillating plate 37 being conventionally disposed in the top 12 near the head portion 15 of the board member 11, and also includes spring members 39 being conventionally connected to the defibrillating plate 37, and further includes a jack 38 being conventionally disposed in one of the side edges 14 of the board member 11 and being connected with wires to the defibrillating plate 37.

In use, the user lays the person upon the top 12 of the board member 11, and secures the strap member 26 about the person's head, and if the need arises the user can use the defibrillating plate 37 to shock the person's heart with the jack 38 receiving a power source, and also if the need arises the user can pivotally raise one or both of the elongate intravenous feeding members 30 to support intravenous feeding members. To keep the person warm, the use can turn on the heating elements 35 by turning on the power switch 40.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A medical backboard apparatus comprising:
    a board assembly including a board member having a top, a bottom, a head portion, and a foot portion, and also having a plurality of hand-hold slots being spaced along a perimeter thereof and being disposed therethrough, said perimeter of said board member including side edges extending along and between said head and foot portions, a portion of a first one of said side edges having a slot formed therein, a notch being formed in said first side edge and extending between said slot and said top of said board member;
    a board support member being attached to said board member;
    a head fastening assembly being connected to said board member for restraining a person's head upon said board member;
    an elongate intravenous fluid support pole having a first end mounted on said first side edge of said board member and having a second end with a hooking means for hooking on an intravenous fluid bag, said first end of said intravenous fluid support pole being pivotally mounted in said slot such that said intravenous fluid support pole is movable between a storage position for storing said pole during periods of non-use and a deployed position for supporting an intravenous fluid bag, said deployed position being characterized by a portion of said intravenous fluid support pole extending from said slot through said notch and being oriented substantially perpendicular to said top of said board member, said storage position being characterized by said intravenous fluid support pole being substantially entirely positioned in said slot and being oriented substantially parallel to said side edge of said board member;
    heating elements including a power line and a power switch being connected to said power line being disposed in said board member; and
    a defibrillating assembly being attached to said board member.

2. A medical backboard apparatus as described in claim 1, wherein said elongate intravenous fluid support pole is pivotable from said storage position to said deployed position without removing said pole from said board member.

3. A medical backboard apparatus as described in claim 1, wherein said foot portion of said board member is tapered toward a foot end thereof, and said head portion includes a multi-sided head edge.

4. A medical backboard apparatus as described in claim 2, wherein said backboard assembly further includes a storage compartment formed in said board member, a cover being removably disposed over said storage compartment, said storage compartment having a slanted bottom wall surface for biasing items in said storage compartment toward one side of said storage compartment.

5. A medical backboard apparatus as described in claim 1, wherein said board support member includes a pair of elongate side support members being attached to said bottom along a side perimeter thereof, and also includes a plurality of cross members being attached to and disposed between said elongate side support members, said cross members being gradually thicker toward said foot portion of said board member.

6. A medical backboard apparatus as described in claim 1, wherein said head fastening assembly includes longitudinal slots being spaced apart and being disposed through said head portion of said board member, and also includes elongate strap support members being disposed in said longitudinal slots, and further includes a strap member having a first end looped about one of said elongate support strap members and also having a second end portion which is looped about another of said elongate strap support members and being fastenable upon itself, and also includes strips of hook and loop fasteners being attached along a portion of said second end portion of said strap member for fastening said strap member upon itself, said strap member being adapted to secure a person's head to said board member.

7. A medical backboard apparatus as described in claim 1, wherein a pair of said elongate intravenous fluid support poles are mounted on opposite said side edges of said board member.

8. A medical backboard apparatus as described in claim 1, wherein said heating elements and said power line are disposed along the perimeter of said board member.

9. A medical backboard apparatus as described in claim 1, wherein said defibrillating assembly includes a defibrillating plate being disposed in said top near said head portion of said board member, and also includes spring members being connected to said defibrillating plate, and further includes a jack being disposed in a side edge of said board member and being connected to said defibrillating plate.

10. A medical backboard apparatus comprising:
    a board assembly including a board member having a top, a bottom, a head portion, and a foot portion, and also having a plurality of hand-hold slots being spaced along a perimeter thereof and being disposed therethrough, said perimeter of said board member including side edges extending along and between said head and foot portions, a portion of a first one of said side edges having a slot formed therein, a notch being formed in said first side edge and extending between said slot and said top of said board member;
    a board support member being attached to said board member;

a head fastening assembly being connected to said board member for restraining a person's head upon said board member;

an elongate intravenous fluid support pole having a first end mounted on said first side edge of said board member and having a second end with a hooking means for hooking on an intravenous fluid bag, said first end of said intravenous fluid support pole being pivotally mounted in said slot such that said intravenous fluid support pole is movable between a storage position for storing said pole during periods of non-use and a deployed position for supporting an intravenous fluid bag, said deployed position being characterized by a portion of said intravenous fluid support pole extending from said slot through said notch and being oriented substantially perpendicular to said top of said board member, said storage position being characterized by said intravenous fluid support pole being substantially entirely positioned in said slot and being oriented substantially parallel to said side edge of said board member;

heating elements including a power line and a power switch being connected to said power line being disposed in said board member; and a defibrillating assembly being attached to said board member;

wherein said elongate intravenous fluid support pole is pivotable from said storage position to said deployed position without removing said pole from said board member;

wherein said foot portion of said board member is tapered toward a foot end thereof, and said head portion includes a multi-sided head edge;

wherein said backboard assembly further includes a storage compartment formed in said board member, a cover being removably disposed over said storage compartment, said storage compartment having a slanted bottom wall surface for biasing items in said storage compartment toward one side of said storage compartment;

wherein said board support member includes a pair of elongate side support members being attached to said bottom along a side perimeter thereof, and also includes a plurality of cross members being attached to and disposed between said elongate side support members, said cross members being gradually thicker toward said foot portion of said board member;

wherein said head fastening assembly includes longitudinal slots being spaced apart and being disposed through said head portion of said board member, and also includes elongate strap support members being disposed in said longitudinal slots, and further includes a strap member having a first end looped about one of said elongate support strap members and also having a second end portion which is looped about another of said elongate strap support members and being fastenable upon itself, and also includes strips of hook and loop fasteners being attached along a portion of said second end portion of said strap member for fastening said strap member upon itself, said strap member being adapted to secure a person's head to said board member;

wherein a pair of said elongate intravenous fluid support poles are mounted on opposite said side edges of said board member;

wherein said heating elements and said power line are disposed along the perimeter of said board member; and wherein said defibrillating assembly includes a defibrillating plate being disposed in said top near said head portion of said board member, and also includes spring members being connected to said defibrillating plate, and further includes a jack being disposed in a side edge of said board member and being connected to said defibrillating plate.

\* \* \* \* \*